(12) United States Patent
Yang et al.

(10) Patent No.: US 11,999,689 B2
(45) Date of Patent: *Jun. 4, 2024

(54) METHOD AND SYSTEM FOR EXTRACTING LONG CHAIN DICARBOXYLIC ACID

(71) Applicants: Cathay Biotech Inc., Shanghai (CN); CIBT America Inc., Newark, DE (US); Cathay (Jinxiang) Biomaterial Co., Ltd., Shandong (CN)

(72) Inventors: Chen Yang, Shanghai (CN); Shuhua Zhang, Shanghai (CN); Yufeng Yang, Shanghai (CN); Xiucai Liu, Shanghai (CN)

(73) Assignees: Cathay Biotech Inc., Shanghai (CN); CIBT America Inc., Newark, DE (US); Cathay (Jinxiang) Biomaterial Co., Ltd., Shandong (CN)

( * ) Notice: Subject to any disclaimer, the term of this patent is extended or adjusted under 35 U.S.C. 154(b) by 161 days.

This patent is subject to a terminal disclaimer.

(21) Appl. No.: 17/551,333

(22) Filed: Dec. 15, 2021

(65) Prior Publication Data

US 2022/0106249 A1    Apr. 7, 2022

Related U.S. Application Data

(63) Continuation-in-part of application No. 16/887,153, filed on May 29, 2020, now Pat. No. 11,229,881.

(30) Foreign Application Priority Data

Dec. 19, 2019 (CN) .......................... 201911320839.2

(51) Int. Cl.
 C07C 51/43     (2006.01)
 C07C 55/02     (2006.01)

(52) U.S. Cl.
 CPC .............. *C07C 51/43* (2013.01); *C07C 55/02* (2013.01); *C07B 2200/13* (2013.01)

(58) Field of Classification Search
 CPC ................. B01D 61/145; B01D 61/58; B01D 2311/2642; C12P 7/44
 See application file for complete search history.

(56) References Cited

U.S. PATENT DOCUMENTS

| | | | |
|---|---|---|---|
| 2013/0096343 | A1 | 4/2013 | Tietz et al. |
| 2013/0116471 | A1 | 5/2013 | Yan et al. |
| 2017/0217871 | A1 | 8/2017 | Schutze et al. |
| 2018/0290961 | A1 | 10/2018 | Schütze et al. |

FOREIGN PATENT DOCUMENTS

| | | |
|---|---|---|
| CN | 1570124 A | 1/2005 |
| CN | 1887843 A | 1/2007 |
| CN | 102329224 A | 1/2012 |
| CN | 102476987 A | 5/2012 |
| CN | 102775292 A | 11/2012 |
| CN | 102976917 A | 3/2013 |
| CN | 103570525 A | 2/2014 |
| CN | 104862348 A | 8/2015 |
| CN | 108017535 A | 5/2018 |
| CN | 110272341 A | 9/2019 |
| CN | 108017535 B | 9/2020 |
| CN | 211445569 U | 9/2020 |
| DE | 102015216815 A1 | 3/2017 |
| JP | S64016743 A | 1/1989 |
| JP | 2000169426 A | 6/2000 |
| JP | 2000302724 A | 10/2000 |
| JP | 2012180306 A | 9/2012 |
| JP | 2013079224 A | 5/2013 |
| JP | 2013529603 A | 7/2013 |
| JP | 2021098685 A | 7/2021 |
| JP | 7209668 B2 | 1/2023 |

OTHER PUBLICATIONS

Extended European Search Report dated Nov. 12, 2020 in related EP Application No. 20178388.3; 9 pgs.
Schutze, Joachim et al., Machine Translation of DE102015216815A1, Feb. 3, 2017 (18 pages).
Japanese Office Action issued in JP2022-164833 dated Sep. 19, 2023.
Second Office Action for Japanese Patent Application No. 2022-164833 with English translation.
First Office Action for Chinese Patent Application No. 2019113208392 with English translation.

*Primary Examiner* — Bradley R Spies
(74) *Attorney, Agent, or Firm* — Fox Rothschild LLP

(57) ABSTRACT

The present disclosure provides a method for extracting long chain dicarboxylic acid, the method comprising: (1) subjecting a long chain dicarboxylic acid fermentation broth to a primary membrane filtration treatment to give a first filtrate; subjecting the first filtrate to decolorization, crystallization, and solid-liquid separation to give a first solid; (2) redissolving the first solid in water to form a solution; subjecting the solution to decolorization, crystallization by acidification, and solid-liquid separation to give a second solid. By the method, the resulted long chain dicarboxylic acid product has a high purity and no residual organic solvent.

14 Claims, No Drawings

METHOD AND SYSTEM FOR EXTRACTING LONG CHAIN DICARBOXYLIC ACID

CROSS REFERENCE TO RELATED APPLICATIONS

This application is a continuation-in-part of U.S. application Ser. No. 16/887,153, filed on May 29, 2020, which claims priority to Chinese Patent Application No. 201911320839.2, filed on Dec. 19, 2019. These applications are hereby incorporated by reference.

TECHNICAL FIELD

The present disclosure relates to long chain dicarboxylic acids, and specifically to a method and a system for extracting long chain dicarboxylic acids produced by biological fermentation.

BACKGROUND ART

Long chain dicarboxylic acids (LCDAs, abbreviated as DCn, n=9-18) are a group of important organic intermediates, which are widely used in fields such as chemical engineering, light industry, agricultural chemicals, medicine and new materials. Long chain dicarboxylic acids do not occur naturally, and normally may be obtained through chemical synthesis and biological fermentation. Chemical synthesis suffers from long synthesis route and strict reaction conditions, and there are only limited types of chemically synthesized long chain dicarboxylic acids, such as dodecanedioic acid. Currently, the most conventional method for preparing long chain dicarboxylic acid is biological fermentation of long carbon chain alkane, fatty acid, fatty acid ester or fatty acid salt in the presence of a specific strain. The technologies for extracting and purifying long chain dicarboxylic acid also affect the quality and cost of the final industrially produced dicarboxylic acid.

CN102476987A discloses a method for refining long chain dicarboxylic acids by combining ultrafiltration and liquid-liquid extraction, in which the fermentation broth from the fermentation section is filtered through a microfiltration membrane to remove solid particles; the filtrate is first filtered through an organic ultrafiltration membrane with a molecular flux of 3,000 to 50,000 Daltons to remove a part of the protein and pigment; then the ultrafiltrate and extractant (one or more C4-C12 monoalcohols) are mixed, heated and acidified; the pH and the temperature are controlled at certain levels, while the extractant and the ultrafiltrate are mixed and stirred for a certain time; then liquid-liquid separation is carried out; the extracted phase is cooled and crystallized; after removing the solvent, a purified product is obtained.

Use of organic solvent in the above purification process leads to residual solvent in the wet crystals, which requires a solvent recovery device during the drying process. Meanwhile, the solvent in the product cannot be completely removed during the drying process, thereby affecting the final performance of the product. Moreover, the organic solvent is volatile and easily lost, which lead to relatively high costs.

In addition, in the existing processes for refining long chain dicarboxylic acid from the fermentation broth, the fermentation substrate, i.e. alkane, is usually difficult to be removed by conventional filtration or centrifugation, because the residual alkane in the fermentation broth exists in a liquid form, and the molecular size thereof is similar to that of the long chain dicarboxylic acid. Sometimes, it forms emulsified droplets with the complex components in the system, or is adsorbed on solid substances in the system, making it difficult to be removed by conventional means such as centrifugation.

If long chain dicarboxylic acid product has high contents of impurities such as ash, nitrogen-containing compounds, alkanes, organic solvents and heteroacids, then in the preparation of polyamide using the dicarboxylic acid as the starting material, these impurities will affect the polymerization of dicarboxylic acid and diamine, thereby affecting the performance of the prepared polyamide. For example, when the content of heteroacids (e.g., monocarboxylic acid) is high, the degree of polymerization of the prepared polyamide cannot reach the theoretical value, and the molecular weight, the viscosity number and the flowability of the polyamide resin deviate from expectations. Furthermore, since the polymerization of dicarboxylic acid and diamine is carried out under high temperature and high pressure conditions, the presence of nitrogen-containing compounds is likely to cause side reactions, producing chromophores, which in turn leads to chromatism of the polyamide products.

In summary, most of the existing processes for purifying long chain dicarboxylic acids from fermentation broth suffer from complex processes, and the dicarboxylic acid products have high contents of impurities including residual alkane and solvent, which may affect the performances of the polyamides products prepared from the dicarboxylic acids.

SUMMARY OF INVENTION

The present disclosure provides a method for extracting long chain dicarboxylic acid, comprising the following steps:
(1) subjecting the long chain dicarboxylic acid fermentation broth to a primary membrane filtration treatment to give a first filtrate; subjecting the first filtrate to decolorization, crystallization, and solid-liquid separation to give a first solid;
(2) redissolving the first solid in water to form a solution; subjecting the solution to decolorization, crystallization by acidification, and solid-liquid separation to give a second solid.

The present disclosure further provides a long chain dicarboxylic acid obtainable by the above method.

By using the method for extracting long chain dicarboxylic acid according to one embodiment of the present disclosure, the obtained long chain dicarboxylic acid products have high purity, extremely low residual alkane, and no residual organic solvent.

SPECIFIC EMBODIMENTS

Typical embodiments reflecting the features and advantages of the present disclosure will be detailed in the description below. It shall be understood that the present disclosure may have various changes in different embodiments, without departing from the scope of the present disclosure, and the description and figures therein are illustrative in nature, not limiting the present disclosure. In the description, the terms "primary", "secondary", "tertiary", "first", "second", "third", etc., are used to distinguish a variety of processes or products with the same names, not limiting thereto.

An embodiment of the present disclosure provides a method for extracting long chain dicarboxylic acid from a long chain dicarboxylic acid fermentation broth, said method comprising:

(1) subjecting the long chain dicarboxylic acid fermentation broth to a primary membrane filtration treatment to give a first filtrate; subjecting the first filtrate to decolorization, crystallization by acidification, and solid-liquid separation to give a first solid;

(2) redissolving the first solid in water to form a solution; subjecting the solution to decolorization, crystallization by acidification, and solid-liquid separation to give a second solid. In an embodiment, said method further comprises step (3) of mixing the second solid and water to form a mixture; subjecting the mixture to a thermostatic treatment at a temperature of 80 to 150° C., preferably 95 to 150° C., more preferably 105-150° C., followed by cooling for crystallization and solid-liquid separation.

In the present disclosure, the long chain dicarboxylic acid fermentation broth may be a fermentation broth obtained by microbial fermentation using alkane, fatty acid or a derivative thereof as the substrate; and the microorganism converts the terminal methyl group of alkane, fatty acid or fatty acid derivative to carboxyl group through oxidation, so as to produce long chain dicarboxylic acid.

In an embodiment, the long chain dicarboxylic acid is a $C_9$-$C_{18}$ dicarboxylic acid.

In an embodiment, the long chain dicarboxylic acid is a linear saturated or non-saturated dicarboxylic acid.

In an embodiment, the long chain dicarboxylic acid may be one or more of azelaic acid, sebacic acid, undecandioic acid, dodecanedioic acid, tridecandioic acid, tetradecandioic acid, pentadecandioic acid, hexadecandioic acid, heptadecandioic acid, octadecandioic acid and 9-octadecene diacid.

In an embodiment, the long chain dicarboxylic acid fermentation broth may be heated to 50-100° C., preferably 70-90° C., before being subjected to the primary membrane filtration.

In an embodiment, before the primary membrane filtration, the temperature of the long chain dicarboxylic acid fermentation broth may be 65° C., 68° C., 72° C., 74° C., 75° C., 76° C., 78° C., 80° C., 82° C., 84° C., 85° C., 86° C., 88° C., 90° C., 92° C., 95° C., 96° C., or 98° C.

In an embodiment, the long chain dicarboxylic acid fermentation broth may be adjusted to a pH of 6.0-12, preferably to 6-11 or 8-11, to dissolve long chain dicarboxylic acid, before being subjected to the primary membrane filtration.

In an embodiment, before being subjected to the primary membrane filtration, the long chain dicarboxylic acid fermentation broth may have a pH of 6, 6.2, 6.5, 7, 7.5, 7.8, 8.2, 8.4, 8.5, 8.6, 8.8, 9.0, 9.2, 9.4, 9.5, 9.8, 10, 10.2, 10.4, 10.5, 10.6, 10.8, 11.0, 11.2, 11.5, 11.6, or 11.8.

In an embodiment, the pH of the fermentation broth may be adjusted by adding a base, including, but not limited to, sodium hydroxide and/or potassium hydroxide.

In an embodiment, the temperature for the primary membrane filtration is 50-100° C., preferably 60-100° C., e.g., 50° C., 52° C., 55° C., 58° C., 60° C., 62° C., 64° C., 65° C., 66° C., 68° C., 70° C., 72° C., 75° C., 78° C., 80° C., 82° C., 85° C., 88° C., 90° C., 92° C., 95° C., or 98° C.

In an embodiment, the primary membrane filtration is a microfiltration membrane filtration or an ultrafiltration membrane filtration. With the primary membrane filtration, most of the impurities such as alkane, cellular tissue of the fermentation microorganism, or pigment in the fermentation broth can be removed.

In an embodiment, during the primary membrane filtration, the pressure difference across the membrane is 0.05-0.6 MPa, e.g., 0.06 MPa, 0.08 MPa, 0.1 MPa, 0.2 MPa, 0.3 MPa, or 0.4 MPa.

In an embodiment, the crystallization in step (1) is selected from any one of crystallization by acidification, cooling for crystallization, and evaporation for crystallization. Further, the pH value of the solution to be crystallized is adjusted to 2 to 5.5, preferably 2.5 to 4 during the crystallization by acidification. Further, the final temperature of the cooling for crystallization is 25 to 65° C., preferably 25 to 48° C.

In an embodiment, step (2) comprises subjecting the solution to a secondary membrane filtration prior to decolorization to form a second filtrate, and said second filtrate is used to perform decolorization in step (2).

In an embodiment, in step (2), subjecting said second filtrate to a tertiary membrane filtration prior to said decolorization to form a third filtrate, said third filtrate is used to perform decolorization in step (2).

In an embodiment, in step (2), a tertiary membrane filtration is carried out after the decolorization and before the crystallization by acidification to form a third filtrate, said third filtrate is used to perform the crystallization by acidification.

The impurities which are different from the dicarboxylic acid in their crystalline structure or solubility may be removed by the crystallization by acidification process. The crystallized long chain dicarboxylic acid solid is re-dissolved, and the distribution and type of the impurities in the long chain dicarboxylic acid solution change. This, in combination with ultrafiltration membrane filtration, can remove those impurities which cannot be removed by simple multi-stage filtration.

In an embodiment, the secondary membrane filtration is microfiltration membrane filtration or ultrafiltration membrane filtration.

In an embodiment, the temperature of the secondary membrane filtration is 20-100° C., preferably 20-45° C., more preferably 30-40° C., e.g., 22° C., 24° C., 25° C., 26° C., 28° C., 30° C., 32° C., 34° C., 35° C., 36° C., 38° C., 39° C., 41° C., 42° C., or 44° C.

In an embodiment, the method further comprises a tertiary membrane filtration which is carried out after the primary membrane filtration and the secondary membrane filtration.

In an embodiment, said method further comprises a fourth membrane filtration after the tertiary membrane filtration, the fourth membrane filtration is microfiltration membrane filtration or ultrafiltration membrane filtration.

In an embodiment, the tertiary membrane filtration is microfiltration membrane filtration or ultrafiltration membrane filtration, preferably ultrafiltration membrane filtration.

In an embodiment, the temperature of the tertiary membrane filtration is 20-100° C., preferably 20-45° C., more preferably 30-40° C., e.g., 22° C., 24° C., 25° C., 26° C., 28° C., 30° C., 32° C., 34° C., 35° C., 36° C., 38° C., 39° C., 41° C., 42° C., or 44° C.

In an embodiment, the pore size of the microfiltration membrane is 0.01-1 μm, preferably 0.01-0.2 μm, more preferably 0.05-0.1 μm.

In an embodiment, the cut-off molecular weight of the ultrafiltration membrane is 1000-200000 Da, preferably 2000-100000 Da, more preferably 2000-50000 Da, even more preferably 2000-20000 Da, e.g., 3000 Da, 5000 Da, 10000 Da, or 50000 Da.

In an embodiment, the ultrafiltration membrane includes, but is not limited to ceramic membrane, polypropylene membrane, polysulfone membrane and polyethersulfone membrane.

In an embodiment, the decolorization treatment is carried out by contacting the liquid to be decolorized (e.g., the filtrate after secondary membrane filtration or the filtrate after tertiary membrane filtration) with a decolorant.

In an embodiment, the decolorization treatment may include solid-liquid mixing of the liquid to be decolorized and a solid decolorant for carrying out the decolorization. Furthermore, the decolorization effect may be improved by stirring the solid-liquid mixture. After the decolorization of the filtrate, the decolorant may be removed by filtration, such as plate-and-frame filtration. The amount of the decolorant used may be 0.05-5 wt %, preferably 0.2-4 wt %, e.g., 0.5 wt %, 3.0 wt %, or 3.5 wt %, in respect of the mass of the filtrate.

Calculated as long chain dicarboxylic acid, the concentration of the filtrate after each stage of membrane filtration is controlled at 2-10 wt %, preferably 2-8 wt %, e.g., 3 wt %, or 6 wt %. Control of the concentration of the filtrate may be realized by dilution or concentration.

In another embodiment, the liquid to be decolorized may be allowed to flow through the decolorant, and the decolorized solution is obtained by collecting the effluent.

In an embodiment, the decolorant includes, but is not limited to, powdered activated carbon, particulate activated carbon, activated carbon fiber, activated clay and diatomite.

In an embodiment, the temperature of the decolorization treatment is 50-100° C., preferably 60-80° C., e.g., 65° C., 70° C., 75° C., 80° C., 85° C., 90° C., or 95° C.

In an embodiment, the duration of the decolorization treatment is 10-180 min, preferably 15-120 min, e.g., 20 min, 25 min, 30 min, 40 min, 50 min, 60 min, 80 min, 100 min, or 150 min.

In an embodiment, the solid-liquid separation in steps (1) to (3) may be centrifugation, or filtration.

In an embodiment, the filtrate obtained by the solid-liquid separation in steps (1) and (2) may be treated to recover inorganic salts, so as to be used as the cultural media for the fermentation process to prepare the dicarboxylic acid. In addition to sodium sulfate, potassium sulfate or potassium nitrate, the filtrate may also comprise impurities such as pigments and organic acids. It should be deprived of the impurities and refined to give crystals of sodium sulfate, potassium sulfate or potassium nitrate, which may be directly used as additives in chemical engineering or agriculture. The obtained sodium sulfate, potassium sulfate or potassium nitrate salt may be subjected to bipolar membrane electrolysis to give the corresponding acid and base, which can be reused in the process for producing long chain dicarboxylic acid, so as to realize comprehensive utilization of the resource and recycled economy and to reduce the emission.

In an embodiment, the crystallization by acidification treatment in steps (1) and (2) includes adjusting the pH of solution after the decolorization of the filtrate to 2-5.5, preferably 2.5-4, e.g., 2.2, 2.5, 2.8, 3.0, 3.2, 3.5, 3.7, 3.8, 4.0, 4.2, 4.3, 4.5, 4.7, or 5.2, followed by crystallization.

In an embodiment, the pH of the filtrate is adjusted by adding an acid, which may be an inorganic acid and/or organic acid.

In an embodiment, the inorganic acid includes, but is not limited to, hydrochloric acid, sulfuric acid, nitric acid; and the organic acid includes, but is not limited to, acetic acid.

In an embodiment, the first solid has a water content of 3-10 wt %, e.g., 5 wt %, 7 wt %, or 8 wt %.

In an embodiment, the first solid or the second solid, before being dispersed in water, may be washed with water.

In step (2) of an embodiment, a base is added into water to facilitate the dissolution of the first solid, in which the base includes, but is not limited to, sodium hydroxide and/or potassium hydroxide.

In step (2) of an embodiment, during the process of adding the base to dissolve the first solid, heating and stirring may be applied to facilitate the dissolution of the first solid.

In step (2) of an embodiment, the first solid may be mixed with an aqueous solution of a base to facilitate the dissolution of the first solid.

In step (2) of an embodiment, a tertiary membrane filtration may be carried out after the decolorization of the filtrate and before the crystallization by acidification.

In step (3) of an embodiment, the mass ratio of the second solid and water may be 1:(2-20), preferably 1:(3-15), more preferably 1:(3-10).

In step (3) of an embodiment, the temperature of the thermostatic treatment is 120-140° C. In step (3) of an embodiment, the temperature of the thermostatic treatment may be 106° C., 108° C., 109° C., 110° C., 112° C., 114° C., 115° C., 116° C., 118° C., 120° C., 122° C., 124° C., 125° C., 126° C., 128° C., 130° C., 132° C., 133° C., 135° C., 136° C., 138° C., 139° C., 140° C., 142° C., 145° C., 146° C., or 148° C.

In step (3) of an embodiment, the duration of the thermostatic treatment is 15-150 min, preferably 30-90 min, e.g., 20 min, 30 min, 40 min, 50 min, 60 min, 70 min, 80 min, 100 min, or 120 min.

In step (3) of an embodiment, after the thermostatic treatment, the final temperature of the cooling process is 25-65° C., preferably 30-50° C., e.g., 28° C., 32° C., 34° C., 35° C., 36° C., 38° C., 40° C., 42° C., 44° C., 45° C., 46° C., 48° C., 50° C., 52° C., 55° C., 58° C., 60° C., 62° C.

In step (3) of an embodiment, after the thermostatic treatment, the mixture is first cooled to 85-115° C., then to the final temperature. For example, the mixture is first cooled to 88° C., 90° C., 92° C., 95° C., 98° C., 100° C., 105° C., 108° C., 110° C., 112° C., or 114° C., then to the final temperature.

In step (3) of an embodiment, after the thermostatic treatment, the mixture is first cooled to 97-115° C. (first cooling stage), e.g., 98° C., 99° C., 100° C., 105° C., 108° C., 110° C., 112° C., or 114° C.; then to 85-95° C. (second cooling stage), e.g., 88° C., 90° C., 91° C., 93° C., or 94° C.; and then to the final temperature (third cooling stage). Furthermore, the average cooling rate in the first cooling stage is 0.5-12° C./h, preferably 0.5-8° C./h, e.g., 3° C./h, 5° C./h, 6° C./h, 10° C./h, 12° C./h, or 14° C./h. The average cooling rate in the second cooling stage is 2-15° C./h, preferably 2-8° C./h, e.g., 3° C./h, 5° C./h, 6° C./h, 10° C./h, 12° C./h, or 14° C./h. The average cooling rate in the third cooling stage is 12-25° C./h, preferably 16-20° C./h, e.g., 12.5° C./h, 13° C./h, 14° C./h, 15° C./h, 16° C./h, 17° C./h, 18° C./h, or 19° C./h.

By controlling the cooling process in step (3), the difference in the properties of the impurities and the dicarboxylic acid crystal is utilized. On one hand, the dissolution of the impurities at elevated temperature is controlled by the thermodynamics, such as the difference in the solubility, so that the impurities remain in water. On the other hand, by programed cooling, there is a difference in the crystal growing rate of the impurities and the dicarboxylic acid. In other words, the crystallization/precipitation dynamic rate is controlled, so that the dicarboxylic acid crystals and the impurities are further separated. After cooling to the final temperature and subjecting to solid-liquid separation, the purity of the dicarboxylic acid product can be further improved.

In an embodiment, the filtrate obtained by the solid-liquid separation in step (3) may be used for dissolving the first solid in step (2).

In the method for extracting long chain dicarboxylic acid according to an embodiment of the present disclosure, by adjusting the process parameters such as temperature in some steps, the long chain dicarboxylic acid product may have undetectable residual alkane and lower contents of impurities, thereby improving the quality of the long chain dicarboxylic acid product and subsequently prepared polyamide product.

The method for extracting long chain dicarboxylic acid according to an embodiment of the present disclosure can overcome the problems of low product quality and environmental pollution resulted from crystallization from organic solvents, and is suitable for the extraction and purification of long chain dicarboxylic acid prepared by biological fermentation.

In an embodiment of the present disclosure, by utilizing two-stage or more than two stage-membrane filtration, dissolution by base/precipitation by acid, and high temperature crystallization, the resulted dicarboxylic acid product has a high purity, white color, low ash content, low metal content, low nitrogen content, no residual organic solvent, and very low or no residual alkane, thereby improving the quality of the long chain dicarboxylic acid product and subsequently prepared polyamide product.

An embodiment of the present disclosure provides a long chain dicarboxylic acid which is obtained by the above extraction method.

In the following, the method for extracting long chain dicarboxylic acid according to an embodiment of the present disclosure is described in detail by way of specific examples, in which the raw materials used, without otherwise specified, are all commercially available, and the test methods are as follows:

1. Gas Chromatographic Test of Long Chain Dicarboxylic Acid

A standard long chain dicarboxylic acid sample was used as the control, and GB5413.27-2010 "Determination of fatty acids in foods for infants and young children, milk and milk products" is referred to.

2. Ash content test A test sample was calcined in a crucible, then in a muffle furnace at 700-800° C. for 2 hours. After cooling to constant weight, the weight was measured, and the weight percentage was calculated.

3. Total Nitrogen Test

Kjeldahl determination was used.

4. Residual Alkane Test 4.1 Instrument

GC-14C gas chromatograph, column: SPB-1701 30 m×0.25 mm×0.25

4.2 Test Procedure 4.2.1 Methyl Esterification 0.75 g of sample was weighed into a reaction tube, to which were added 5 ml of methanol and 1 ml of 6 mol/L hydrochloric acid solution in methanol. The reaction tube was sealed and heated at 100° C. for 30 min, and then cooled to room temperature. 3 g of solid sodium bicarbonate was added and reacted until no bubble was evolved. The mixture was allowed to stand still to give a clear liquid, to which was slowly added sodium bicarbonate to neutralize the solution until no $CO_2$ gas was evolved.

4.2.2 Residual Alkane Test 1 ml of methyl esterified sample was injected into GC-14C gas chromatograph with a 0.45 μm syringe filter. The residual alkane was calculated by area normalization method.

5. Light Transmittance Test

Substances with different colors have different light transmittances and absorption properties at a certain wavelength. Based on this, the color of the dicarboxylic acid product is represented by the light transmittance of a 25% solution of the dicarboxylic acid sample in dimethyl sulfoxide at 440 nm.

6. Test of the Yellow Index (YI) of Polyamide

Yellow index is the yellow value determined using International Commission on Illumination (CIE) standard C light source and using magnesium oxide as the reference. Yellow index YI is calculated as follows:

$$YI=(100(1.28X-1.06Z))/Y$$

in which, X, Y and Z are the determined tristimulus values, respectively.

It is determined with a yellow indexer, the test temperature is 25±5° C.; and the relative humidity is 50±20%.

Test Procedure:

For a transparent sample, its spectral transmittance relative to air was determined (transmission method); for a non-transparent or semi-transparent sample, the spectral reflectivity relative to a standard whiteboard or a working whiteboard was determined (reflection method), the background being a white working board; powdered or particulate sample should be tested from the bottom with reflection method in a glass container, which is covered with a back cover to avoid the influence of outside light.

The spectral tristimulus values X, Y and Z of the test sample relative to the standard C light source were determined by automatic integration of the instrument.

Colorimeter and color difference meter, both color filer type tristimulus value color instruments, may be used to directly read the X, Y and Z values.

For homogeneous plastic, the diameter of the measuring aperture should be >12 mm; for non-homogeneous plastic, the diameter of the measuring aperture should be >10 mm.

Example A

Following the fermentation method disclosed in Example 7 of CN110218746A, a dodecanedioic acid fermentation broth was obtained.

(1) To the dodecanedioic acid fermentation broth was added a base to adjust the pH to 6.3. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 5.7 wt %. The filtrate was thermostatically decolorized at 90° C. with 2.5 wt % activated carbon for 25 min, and filtered to give a clear solution The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered with an ultrafiltration membrane having a cut-off molecular weight of 3000 Da at a temperature of 35° C.

Calculated as dodecanedioic acid, the concentration of the filtrate after filtration with the ultrafiltration membrane was controlled at 5.7 wt %. The filtrate was decolorized at 90° C. with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 120° C. for 65 min, then cooled to 100° C. in 4 h, and to 90° C. in 2 h, and further to 40° C. in 4 h. Crystals were precipitated and filtered to give a solid, which was dried to give the dodecanedioic acid product.

Example B

Following the fermentation method disclosed in Example 7 of CN110218746A, a dodecanedioic acid fermentation broth was obtained.

(1) the pH value of the dodecanedioic acid fermentation broth was adjusted to 6.1. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 9.5 wt %. The filtrate was thermostatically decolorized at 90° C. with 2.5 wt % activated carbon for 25 min, and filtered to give a clear solution The clear solution obtained by the decolorization treatment is cooled to 35° C. for crystallization, filtered to give a first solid.

(2) The first solid (water content, 2.7 wt %) was added into water. Sodium hydroxide was added to dissolve the first solid. The mixture was filtered with an ultrafiltration membrane having a cut-off molecular weight of 3000 Da at a temperature of 35° C.

Calculated as dodecanedioic acid, the concentration of the filtrate after filtration with the ultrafiltration membrane was controlled at 5.7 wt %. The filtrate was decolorized at 90° C. with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 120° C. for 68 min, then cooled to 100° C. in 4 h, and to 90° C. in 2 h, and further to 40° C. in 4 h. Crystals were precipitated and filtered to give a solid, which was dried to give the dodecanedioic acid product.

Example C

Following the fermentation method disclosed in Example 3 of CN1570124A, a dodecanedioic acid fermentation broth was obtained.

(1) To the dodecanedioic acid fermentation broth was added a base to adjust the pH to 9.7. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 5.7 wt %. The filtrate was thermostatically decolorized at 90° C. with 2.5 wt % activated carbon for 25 min, and filtered to give a clear solution The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered with an ultrafiltration membrane having a cut-off molecular weight of 3000 Da at a temperature of 35° C.

Calculated as dodecanedioic acid, the concentration of the filtrate after filtration with the ultrafiltration membrane was controlled at 5.7 wt %. The filtrate was decolorized at 90° C. with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 95° C. for 80 min, then cooled to 100° C. in 4 h, and to 90° C. in 2 h, and further to 40° C. in 4 h. Crystals were precipitated and filtered to give a solid, which was dried to give the dodecanedioic acid product.

Example D

Following the fermentation method disclosed in Example 4 of CN1570124A, a dodecanedioic acid fermentation broth was obtained.

(1) To the dodecanedioic acid fermentation broth was added a base to adjust the pH to 9.7. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 5.7 wt %. The filtrate was thermostatically decolorized at 90° C. with 2.5 wt % activated carbon for 25 min, and filtered to give a clear solution The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered with a ceramic microfiltration membrane having a pore size of 0.05 μm at a temperature of 80° C., and the pressure difference across the membrane was 0.3 MPa.

Calculated as dodecanedioic acid, the concentration of the filtrate after filtration with the microfiltration membrane was controlled at 5.7 wt %. The filtrate was decolorized at 90° C.

with 2.5 wt % activated carbon for 25 min, and filtered with a plate-and-frame filter to give the decolorized liquid.

The decolorized liquid was filtered with an ultrafiltration membrane having a cut-off molecular weight of 3000 Da at a temperature of 35° C.

The filtrate was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 120° C. for 60 min, then cooled to 100° C. in 4 h, and to 90° C. in 2 h, and further to 40° C. in 4 h. Crystals were precipitated and filtered to give a solid, which was dried to give the dodecanedioic acid product.

Example E

Following the fermentation method disclosed in Example 4 of CN1570124A, a dodecanedioic acid fermentation broth was obtained.

(1) To the dodecanedioic acid fermentation broth was added a base to adjust the pH to 9.7. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 5.7 wt %. The filtrate was thermostatically decolorized at 90° C. with 2.5 wt % activated carbon for 25 min, and filtered to give a clear solution The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered with an ultrafiltration membrane having a cut-off molecular weight of 3000 Da at a temperature of 35° C.

Calculated as dodecanedioic acid, the concentration of the filtrate after filtration with the ultrafiltration membrane was controlled at 5.7 wt %. The filtrate was decolorized at 90° C. with 2.5 wt % activated carbon for 25 min, and filtered with a plate-and-frame filter to give the decolorized liquid.

The decolorized liquid was filtered with an ultrafiltration membrane having a cut-off molecular weight of 3000 Da at a temperature of 35° C.

The filtrate was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 120° C. for 60 min, then cooled to 100° C. in 4 h, and to 90° C. in 2 h, and further to 40° C. in 4 h. Crystals were precipitated and filtered to give a solid, which was dried to give the dodecanedioic acid product.

Example F

Following the fermentation method disclosed in Example 4 of CN1570124A, a dodecanedioic acid fermentation broth was obtained.

(1) To the dodecanedioic acid fermentation broth was added a base to adjust the pH to 9.7. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 5.7 wt %. The filtrate was thermostatically decolorized at 90° C. with 2.5 wt % activated carbon for 27 min, and filtered to give a clear solution The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was sequentially subjected to microfiltration membrane filtration with a ceramic microfiltration membrane at a temperature of 80° C. and ultrafiltration membrane filtration with an ultrafiltration membrane at a temperature of 35° C. The ceramic microfiltration membrane has a pore size of 0.05 μm, and the pressure difference across the membrane was 0.3 MPa, and the ultrafiltration membrane has a cut-off molecular weight of 3000 Da.

Calculated as dodecanedioic acid, the concentration of the filtrate after filtration with the ultrafiltration membrane was controlled at 5.7 wt %. The filtrate was decolorized at 90° C. with 2.5 wt % activated carbon for 25 min, and filtered with a plate-and-frame filter to give the decolorized liquid.

The filtrate was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 120° C. for 60 min, then cooled to 100° C. in 4 h, and to 90° C. in 2 h, and further to 40° C. in 4 h. Crystals were precipitated and filtered to give a solid, which was dried to give the dodecanedioic acid product.

Example G

Following the fermentation method disclosed in Example 4 of CN1570124A, a dodecanedioic acid fermentation broth was obtained.

(1) To the dodecanedioic acid fermentation broth was added a base to adjust the pH to 9.7. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 5.7 wt %. The filtrate was thermostatically decolorized at 90° C. with 2.5 wt % activated carbon for 27 min, and filtered to give a clear solution The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered twice with an ultrafiltration membrane having a cut-off molecular weight of 3000 Da at a temperature of 35° C.

Calculated as dodecanedioic acid, the concentration of the filtrate after filtration with the ultrafiltration membrane was controlled at 5.7 wt %. The filtrate was decolorized at 90° C.

with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 120° C. for 60 min, then cooled to 100° C. in 4 h, and to 90° C. in 2 h, and further to 40° C. in 4 h. Crystals were precipitated and filtered to give a solid, which was dried to give the dodecanedioic acid product.

Example H

Following the fermentation method disclosed in Example 3 of CN1570124A, a dodecanedioic acid fermentation broth was obtained.

(1) To the dodecanedioic acid fermentation broth was added a base to adjust the pH to 9.6. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 5.7 wt %. The filtrate was thermostatically decolorized at 90° C. with 2.5 wt % activated carbon for 25 min, and filtered to give a clear solution The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered with an ultrafiltration membrane having a cut-off molecular weight of 3000 Da at a temperature of 35° C.

Calculated as dodecanedioic acid, the concentration of the filtrate after filtration with the ultrafiltration membrane was controlled at 5.7 wt %. The filtrate was decolorized at 90° C. with 2.5 wt % activated carbon for 25 min, and filtered with a plate-and-frame filter to give the decolorized liquid.

The decolorized liquid was adjusted to pH 2.9 with sulfuric acid for crystallization by acidification, and filtered to give a second solid comprising dodecanedioic acid.

(3) The second solid was added into water with a mass ratio of the second solid to water of 1:10. The mixture was kept at 85° C. for 85 min, then cooled to 100° C. in 4 h, and to 90° C. in 2 h, and further to 40° C. in 4 h. Crystals were precipitated and filtered to give a solid, which was dried to give the dodecanedioic acid product.

Example 1

Following the fermentation method disclosed in Example 4 of CN1570124A, a dodecanedioic acid fermentation broth was obtained.

(1) To the dodecanedioic acid fermentation broth was added a base to adjust the pH to 9.7. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 5.7 wt %. The filtrate was thermostatically decolorized at 90° C. with 2.5 wt % activated carbon for 25 min, and filtered to give a clear solution The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered with an ultrafiltration membrane having a cut-off molecular weight of 3000 Da at a temperature of 35° C.

Calculated as dodecanedioic acid, the concentration of the filtrate after filtration with the ultrafiltration membrane was controlled at 5.7 wt %. The filtrate was decolorized at 90° C. with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 120° C. for 60 min, then cooled to 100° C. in 4 h, and to 90° C. in 2 h, and further to 40° C. in 4 h. Crystals were precipitated and filtered to give a solid, which was dried to give the dodecanedioic acid product.

Example 2

Following the fermentation method disclosed in Example 6 of CN1570124A, a tetradecandioic acid fermentation broth was obtained.

(1) To the tetradecandioic acid fermentation broth was added a base to adjust the pH to 9.0. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.5 MPa.

Calculated as tetradecandioic acid, the concentration of the filtrate after filtration with the microfiltration membrane was controlled at 4.5 wt %. The filtrate was thermostatically decolorized at 90° C. with 2.5 wt % activated carbon for 25 min, and filtered to give a clear solution.

The clear solution of tetradecandioic acid obtained after the decolorization treatment was adjusted to pH 3.0 with sulfuric acid for crystallization by acidification, and filtered to give a first solid comprising tetradecandioic acid.

(2) The first solid (water content, 5 wt %) was added into water. Sodium hydroxide was added to dissolve the first solid. The mixture was filtered with an ultrafiltration membrane having a cut-off molecular weight of 10000 Da at a temperature of 35° C.

Calculated as tetradecandioic acid, the concentration of the filtrate after filtration with the ultrafiltration membrane was controlled at 4.5 wt %. The filtrate was decolorized at 90° C. with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising tetradecandioic acid.

(3) The second solid was added into water with a mass ratio of the second solid to water of 1:10. The mixture was kept at 130° C. for 30 min, then cooled to 100° C. in 5 h, and to 90° C. in 2 h, and further to 40° C. in 4 h. Crystals were precipitated and filtered to give a solid, which was dried to give the tetradecandioic acid product.

Example 3

Following the fermentation method disclosed in Example 8 of CN1570124A, a hexadecandioic acid fermentation broth was obtained.

(1) To the hexadecandioic acid fermentation broth was added a base to adjust the pH to 8.3. The mixture was heated to 80° C., and the fermentation broth was filtered at 80° C. with a ceramic microfiltration membrane to give a filtrate. The ceramic microfiltration membrane has a pore size of 0.1 µm, and the pressure difference across the membrane was 0.2 MPa.

Calculated as hexadecandioic acid, the concentration of the filtrate after filtration with the microfiltration membrane was controlled at 3.7 wt %. The filtrate was thermostatically decolorized at 80° C. with 4 wt % activated carbon for 25 min, and filtered with a plate-and-frame filter to give a clear solution.

The clear solution of hexadecandioic acid obtained after the decolorization treatment was adjusted to pH 3.0 with sulfuric acid for crystallization by acidification, and filtered to give a first solid comprising hexadecandioic acid.

(2) The first solid (water content, 8 wt %) was added into water. Sodium hydroxide was added to dissolve the first solid. The mixture was filtered with an ultrafiltration membrane having a cut-off molecular weight of 5000 Da at a temperature of 35° C.

Calculated as hexadecandioic acid, the concentration of the filtrate after filtration with the ultrafiltration membrane was controlled at 3.7 wt %. The filtrate was decolorized at 90° C. with 2.5 wt % activated carbon for 25 min, and filtered with a plate-and-frame filter to give the decolorized liquid.

The decolorized liquid was adjusted to pH 3.5 with sulfuric acid for crystallization by acidification, and filtered to give a second solid comprising hexadecandioic acid.

(3) The second solid was added into water with a mass ratio of the second solid to water of 1:10. The mixture was kept at 135° C. for 60 min, then cooled to 100° C. in 5 h, and to 90° C. in 1 h, and further to 50° C. in 3 h. Crystals were precipitated and filtered to give a solid, which was dried to give the hexadecandioic acid product.

Example 4

Following the fermentation method disclosed in Example 5 of CN1570124A, a tridecandioic acid fermentation broth was obtained.

(1) To the tridecandioic acid fermentation broth was added a base to adjust the pH to 10.0. The mixture was heated to 90° C., and the fermentation broth was filtered at 90° C. with a ceramic microfiltration membrane to give a filtrate. The ceramic microfiltration membrane has a pore size of 0.05 µm, and the pressure difference across the membrane was 0.5 MPa.

Calculated as tridecandioic acid, the concentration of the filtrate after filtration with the microfiltration membrane was controlled at 5.0 wt %. The filtratewas thermostatically decolorized at 90° C. with 3 wt % activated carbon for 60 min, and filtered to give a clear solution.

The clear solution of tridecandioic acid obtained after the decolorization treatment was adjusted to pH 2.5 with sulfuric acid for crystallization by acidification, and filtered to give a first solid comprising tridecandioic acid.

(2) The first solid (water content, 5 wt %) was added into water. Sodium hydroxide was added to dissolve the first solid. The mixture was filtered with an ultrafiltration membrane having a cut-off molecular weight of 2000 Da at a temperature of 35° C.

Calculated as tridecandioic acid, the concentration of the filtrate after filtration with the ultrafiltration membrane was controlled at 5.0 wt %. The filtrate was decolorized at 90° C. with 3 wt % activated carbon for 40 min, and filtered with a plate-and-frame filter to give the decolorized liquid.

The decolorized liquid was adjusted to pH 2.8 with sulfuric acid for crystallization by acidification, and filtered to give a second solid comprising tridecandioic acid.

(3) The second solid was added into water with a mass ratio of the second solid to water of 1:5. The mixture was kept at 115° C. for 30 min, then cooled to 100° C. in 4 h, and to 90° C. in 2 h, and further to 40° C. in 4 h. Crystals were precipitated and filtered to give a solid, which was dried to give the tridecandioic acid product.

Example 5

Following the fermentation method disclosed in Example 4 of CN1570124A, a dodecanedioic acid fermentation broth was obtained.

(1) To the dodecanedioic acid fermentation broth was added a base to adjust the pH to 9.6. The mixture was heated to 90° C., and the fermentation broth was filtered at 90° C. with a ceramic microfiltration membrane to give a filtrate. The ceramic microfiltration membrane has a pore size of 0.05 µm, and the pressure difference across the membrane was 0.3 MPa.

Calculated as dodecanedioic acid, the concentration of the filtrate after filtration with the microfiltration membrane was controlled at 13.5 wt %. The filtrate was thermostatically decolorized at 90° C. with 2.5 wt % activated carbon for 25 min, and filtered to give a clear solution The clear solution of dodecanedioic acid obtained after the decolorization treatment was adjusted to pH 3 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered with an ultrafiltration membrane having a cut-off molecular weight of 3000 Da at a temperature of 35° C.

Calculated as dodecanedioic acid, the concentration of the filtrate after filtration with the ultrafiltration membrane was controlled at 5.8 wt %. The filtrate was decolorized at 90° C. with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 122° C. for 65 min, then cooled to 15° C. in 5 h. Crystals were precipitated and filtered to give a solid, which was dried to give the dodecanedioic acid product.

Example 6

Following the fermentation method disclosed in Example 6 of CN1570124A, a tetradecandioic acid fermentation broth was obtained.

(1) To the tetradecandioic acid fermentation broth was added a base to adjust the pH to 9.0. The mixture was heated to 90° C., and the fermentation broth was filtered at 90° C. with a ceramic microfiltration membrane to give a filtrate. The ceramic microfiltration membrane has a pore size of 0.05 μm, and the pressure difference across the membrane was 0.5 MPa.

Calculated as tetradecandioic acid, the concentration of the filtrate after filtration with the microfiltration membrane was controlled at 9.6 wt %. The filtrate was thermostatically decolorized at 90° C. with 2.5 wt % activated carbon for 25 min, and filtered to give a clear solution.

The clear solution of tetradecandioic acid obtained after the decolorization treatment was adjusted to pH 4.7 with sulfuric acid for crystallization by acidification, and filtered to give a first solid comprising tetradecandioic acid.

(2) The first solid (water content, 5 wt %) was added into water. Sodium hydroxide was added to dissolve the first solid. The mixture was filtered with an ultrafiltration membrane having a cut-off molecular weight of 50000 Da at a temperature of 35° C.

Calculated as tetradecandioic acid, the concentration of the filtrate after filtration with the ultrafiltration membrane was controlled at 9.6 wt %. The filtrate was decolorized at 90° C. with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising tetradecandioic acid.

(3) The second solid was added into water with a mass ratio of the second solid to water of 1:10. The mixture was kept at 130° C. for 30 min, then cooled to 100° C. in 5 h, and to 90° C. in 2 h, and further to 40° C. in 4 h. Crystals were precipitated and filtered to give a solid, which was dried to give the tetradecandioic acid product.

Example 7

Following the fermentation method disclosed in Example 8 of CN1570124A, a hexadecandioic acid fermentation broth was obtained.

(1) To the hexadecandioic acid fermentation broth was added a base to adjust the pH to 8.3. The mixture was heated to 80° C., and the fermentation broth was filtered at 80° C. with a ceramic microfiltration membrane to give a filtrate The ceramic microfiltration membrane has a pore size of 0.1 μm, and the pressure difference across the membrane was 0.2 MPa.

Calculated as hexadecandioic acid, the concentration of the filtrate after filtration with the microfiltration membrane was controlled at 3.7 wt %. The filtrate was thermostatically decolorized at 80° C. with 4 wt % activated carbon for 25 min, and filtered with a plate-and-frame filter to give a clear solution.

The clear solution of hexadecandioic acid obtained after the decolorization treatment was adjusted to pH 3.0 with sulfuric acid for crystallization by acidification, and filtered to give a first solid comprising hexadecandioic acid.

(2) The first solid (water content, 8 wt %) was added into water. Sodium hydroxide was added to dissolve the first solid. The mixture was filtered with an ultrafiltration membrane having a cut-off molecular weight of 5000 Da at a temperature of 35° C.

Calculated as hexadecandioic acid, the concentration of the filtrate after filtration with the ultrafiltration membrane was controlled at 3.7 wt %. The filtrate was decolorized at 55° C. with 2.5 wt % activated carbon for 40 min, and filtered with a plate-and-frame filter to give the decolorized liquid.

The decolorized liquid was adjusted to pH 4.5 with sulfuric acid for crystallization by acidification, and filtered to give a second solid comprising hexadecandioic acid.

(3) The second solid was added into water with a mass ratio of the second solid to water of 1:10. The mixture was kept at 108° C. for 60 min, then cooled to 100° C. in 4 h, and to 90° C. in 1 h, and further to 60° C. in 2 h. Crystals were precipitated and filtered to give a solid, which was dried to give the hexadecandioic acid product.

Example 8

Following the fermentation method disclosed in Example 5 of CN1570124A, a tridecandioic acid fermentation broth was obtained.

(1) To the tridecandioic acid fermentation broth was added a base to adjust the pH to 10.0. The mixture was heated to 65° C., and the fermentation broth was filtered at 65° C. with a ceramic microfiltration membrane to give a filtrate. The ceramic microfiltration membrane has a pore size of 0.05 μm, and the pressure difference across the membrane was 0.5 MPa.

Calculated as tridecandioic acid, the concentration of the filtrate after filtration with the microfiltration membrane was controlled at 5.0 wt %. The filtrate was thermostatically decolorized at 90° C. with 3 wt % activated carbon for 60 min, and filtered to give a clear solution.

The clear solution of tridecandioic acid obtained after the decolorization treatment was adjusted to pH 4.8 with sulfuric acid for crystallization by acidification, and filtered to give a first solid comprising tridecandioic acid.

(2) The first solid (water content, 5 wt %) was added into water. Sodium hydroxide was added to dissolve the first solid. The mixture was filtered with an ultrafiltration membrane having a cut-off molecular weight of 2000 Da at a temperature of 35° C.

Calculated as tridecandioic acid, the concentration of the filtrate after filtration with the ultrafiltration membrane was controlled at 5.0 wt %. The filtrate was decolorized at 90° C. with 3 wt % activated carbon for 40 min, and filtered with a plate-and-frame filter to give the decolorized liquid.

The decolorized liquid was adjusted to pH 2.8 with sulfuric acid for crystallization by acidification, and filtered to give a second solid comprising tridecandioic acid.

(3) The second solid was added into water with a mass ratio of the second solid to water of 1:5. The mixture was kept at 105° C. for 30 min, then cooled to 90° C. in 1 h, and further to 40° C. in 2 h. Crystals were precipitated and filtered to give a solid, which was dried to give the tridecandioic acid product.

Example 9

Following the fermentation method disclosed in Example 4 of CN1570124A, a dodecanedioic acid fermentation broth was obtained.

(1) To the dodecanedioic acid fermentation broth was added a base to adjust the pH to 9.7. The mixture was heated to 40° C., and the fermentation broth was filtered at 40° C. with a ceramic microfiltration membrane to give a filtrate. The ceramic microfiltration membrane has a pore size of 0.05 μm, and the pressure difference across the membrane was 0.3 MPa.

Calculated as dodecanedioic acid, the concentration of the filtrate after filtration with the microfiltration membrane was controlled at 13.5 wt %. The filtrate was thermostatically decolorized at 90° C. with 2.5 wt % activated carbon for 25 min, and filtered to give a clear solution.

The clear solution of dodecanedioic acid obtained after the decolorization treatment was adjusted to pH 3.0 with sulfuric acid for crystallization by acidification, and filtered to give a first solid comprising dodecanedioic acid.

(2) The first solid (water content, 3 wt %) was added into water. Sodium hydroxide was added to dissolve the first solid. The mixture was filtered with an ultrafiltration membrane having a cut-off molecular weight of 3000 Da at a temperature of 35° C.

Calculated as dodecanedioic acid, the concentration of the filtrate after filtration with the ultrafiltration membrane was controlled at 13.5 wt %. The filtrate was decolorized at 90° C. with 2.5 wt % activated carbon for 25 min, and filtered with a plate-and-frame filter to give the decolorized liquid.

The decolorized liquid was adjusted to pH 2.8 with sulfuric acid for crystallization by acidification, and filtered to give a second solid comprising dodecanedioic acid.

(3) The second solid was added into water with a mass ratio of the second solid to water of 1:10. The mixture was kept at 122° C. for 60 min, then cooled to 15° C. in 5 h. Crystals were precipitated and filtered to give a solid, which was dried to give the dodecanedioic acid product.

Comparative Example

Following the fermentation method disclosed in Example 4 of CN1570124A, a dodecanedioic acid fermentation broth was obtained. The dodecanedioic acid fermentation broth was heated to 90° C., followed by addition of a base to adjust the pH to 8.5 and centrifugation at 90° C. The clear solution obtained was decolorized at 90° C. with 5 wt % activated carbon for 30 min, and filtered with a plate-and-frame filter to give a clear solution. The clear solution was adjusted to pH 3.0 for crystallization by acidification, filtered, and washed to give the dodecanedioic acid product.

Relevant tests were carried out on the products obtained in the above examples and the comparative example, and the results are shown in Table 1.

TABLE 1

| | Performances of the long chain dicarboxylic acid products | | | | | | |
|---|---|---|---|---|---|---|---|
| | Total acid content (%) | Purity(%) | Total nitrogen content (ppm) | Ash content (ppm) | Light transmittance (%) | Residual solvent (ppm) | Residue alkane (ppm) |
| Ex. A | 99.79 | 99.72 | 38 | 23 | 99.2 | Not detected | Not detected |
| Ex. B | 99.90 | 99.81 | 31 | 17 | 99.5 | Not detected | Not detected |
| Ex. C | 99.92 | 99.85 | 34 | 25 | 99.3 | Not detected | Not detected |
| Ex. D | 99.96 | 99.91 | 23 | 15 | 99.6 | Not detected | Not detected |
| Ex. E | 99.96 | 99.89 | 25 | 15 | 99.6 | Not detected | Not detected |
| Ex. F | 99.93 | 99.85 | 28 | 16 | 99.4 | Not detected | Not detected |
| Ex. G | 99.94 | 99.87 | 27 | 17 | 99.5 | Not detected | Not detected |
| Ex. H | 99.35 | 99.12 | 42 | 25 | 99.0 | Not detected | Not detected |
| Ex. 1 | 99.90 | 99.82 | 30 | 18 | 99.3 | Not detected | Not detected |
| Ex. 2 | 99.55 | 98.74 | 40 | 22 | 99.2 | Not detected | Not detected |
| Ex. 3 | 99.20 | 98.60 | 38 | 25 | 99.0 | Not detected | Not detected |
| Ex. 4 | 99.65 | 99.02 | 42 | 26 | 99.1 | Not detected | Not detected |
| Ex. 5 | 99.16 | 98.62 | 53 | 46 | 98.2 | Not detected | Not detected |
| Ex. 6 | 99.37 | 98.56 | 52 | 27 | 99.1 | Not detected | Not detected |
| Ex. 7 | 99.11 | 98.49 | 44 | 80 | 98.7 | Not detected | Not detected |
| Ex. 8 | 98.30 | 97.65 | 67 | 41 | 97.5 | Not detected | Not detected |
| Ex. 9 | 98.26 | 97.40 | 78 | 84 | 97.2 | Not detected | Not detected |
| Comp. Ex. | 99.10 | 98.10 | 179 | 476 | 98.2 | Not detected | 26 |

Application Example

Polyamide 512 and polyamide 513 were prepared using the prepared dodecanedioic acid and tridecandioic acid, respectively, as the starting materials, and the detailed procedure is as follows.

Nitrogen is introduced into a 100 L polymerization vessel (K/SY166-2007 type) to replace the air therein. To the reaction vessel were added 15 kg pure water and then 115.2 mol pentanediamine. After stirring, 115.2 mol dodecanedioic acid or tridecandioic acid was added, and the pH was adjusted to 7.23 (the test results after diluting the salt solution to 10% at 30° C.) to give the aqueous polyamide salt solution.

Under the nitrogen atmosphere, the temperature of the oil bath was gradually increased to 288° C. After the pressure in the polymerization vessel increased to 1.5 MPa, exhaustion was started. When the temperature in the vessel reached 262° C., the vessel was evacuated to −0.07 MPa, which was kept for 35 min, to give polyamide 512 or polyamide 513. The yellow indexes of the resulted polyamide slices were determined, and the results are shown in Tables 2 and 3.

TABLE 2

Yellow indexes of polyamide 512

|  | Yellow Index (YI) |
| --- | --- |
| Ex. D | 2.96 |
| Ex. 1 | 3.10 |
| Ex. 5 | 6.25 |
| Ex. 9 | 9.44 |
| Comp. Ex. | 23.71 |

TABLE 3

Yellow indexes of polyamide 513

|  | Yellow Index (YI) |
| --- | --- |
| Ex. 4 | 3.75 |
| Ex. 8 | 10.24 |

Unless otherwise specified, all the terms used in the present disclosure have the meanings conventionally understood by a person skilled in the art.

The embodiments described in the present disclosure are for the purpose of illustration only, not for limiting the scope of the present disclosure. A person skilled in the art may make various substitutions, changes and modifications within the scope of the present disclosure. Therefore, the scope of the present disclosure is not limited to the above embodiments, but is defined by the appended claims.

The invention claimed is:

1. A method for extracting long chain dicarboxylic acid, comprising:
   (1) subjecting a long chain dicarboxylic acid fermentation broth to a primary membrane filtration treatment to give a first filtrate; subjecting the first filtrate to decolorization, crystallization, and solid-liquid separation to give a first solid;
   (2) redissolving the first solid in water to form a solution;
   (3) subjecting the solution to a secondary membrane filtration treatment to form a second filtrate;
   (4) subjecting the second filtrate to decolorization, crystallization by acidification, and solid-liquid separation to give a second solid,
   wherein the secondary membrane filtration is microfiltration membrane filtration using a micromembrane with a pore size of the microfiltration membrane of 0.01-1 μm or ultrafiltration membrane filtration using an ultrafiltration membrane with a cut-off molecular weight of 2000-50000 Da; and the concentration of the filtrate after the secondary membrane filtration is controlled to be 2 to 10 wt % calculated as the long chain dicarboxylic acid.

2. The method according to claim 1, further comprising step (5) of mixing the second solid and water to form a mixture, subjecting the mixture to a thermostatic treatment at a temperature of 80 to 150° C., preferably 95 to 150° C., more preferably 105 to 150° C., followed by cooling for crystallization, and solid-liquid separation.

3. The method according to claim 1, wherein the crystallization in step (1) is selected from any one of crystallization by acidification, cooling for crystallization, and evaporation for crystallization.

4. The method according to claim 3, wherein the pH value of the solution to be crystallized is adjusted to 2 to 5.5, preferably 2.5 to 4 during the crystallization by acidification; and/or
   the final temperature of the cooling for crystallization is 25 to 65° C., preferably 25 to 48° C.

5. The method according to claim 1, wherein in step (1), prior to the primary membrane filtration, the pH of the long-chain dicarboxylic acid fermentation broth is controlled to be 6.0 to 12; and/or
   the primary membrane filtration in step (1) is microfiltration membrane filtration or ultrafiltration membrane filtration; and/or
   the filtration membrane for primary membrane filtration in step (1) includes a ceramic membrane, polypropylene membrane, polysulfone membrane, polyether sulfone membrane; and/or
   the temperature for the primary membrane filtration in step (1) is 50 to 100° C., and the pressure difference across the membrane is 0.05 to 0.6 MPa; and/or
   the concentration of the filtrate after the primary membrane filtration in step (1) is controlled to be 2 to 10 wt %; and/or,
   in step (1) and step (2), the temperature for the decolorization is 50 to 100° C.; and/or,
   in step (1) and step (2), the solid-liquid separation may be centrifugal separation, filtration separation; and/or,
   in step (2), a base may be added to promote the dissolution of the first solid during the process of redissolving the first solid in water to form a solution; and/or,
   in step (2), the pH value of the solution to be crystallized is adjusted to 2 to 5.5, preferably 2.5 to 4, during the crystallization by acidification.

6. The method according to claim 1, wherein, in step (2), subjecting said second filtrate to a tertiary membrane filtration prior to said decolorization to form a third filtrate, said third filtrate is used to perform decolorization in step (2); and/or
   in step (2), a tertiary membrane filtration is carried out after the decolorization and before the crystallization by acidification to form a third filtrate, said third filtrate is used to perform the crystallization by acidification.

7. The method according to claim 1, wherein the temperature for the secondary membrane filtration is 20 to 100° C.

8. The method according to claim 6, wherein the tertiary membrane filtration is microfiltration membrane filtration or ultrafiltration membrane filtration; and/or,
   the temperature for the tertiary membrane filtration is 20 to 100° C., preferably 20 to 45° C.; and/or
   the concentration of the filtrate after the tertiary membrane filtration is controlled to be 2 to 10 wt %.

9. The method according to claim 2, wherein, in step (5), the mass ratio of the second solid to water is 1:(2 to 10), preferably 1:(3 to 15), more preferably 1:(3 to 10); and/or
   in step (5), the temperature for the thermostatic treatment is 120 to 140° C.; and/or
   the final temperature of the cooling for crystallization is 25 to 65° C.

10. The method according to claim 1, wherein, in step (5), after the thermostatic treatment, the mixture is first cooled to 97 to 115° C., the average cooling rate is 0.5 to 12° C./h, preferably 0.5 to 8° C./h; cooled further to 85 to 95° C., the average cooling rate is 2 to 15° C./h, preferably 2 to 8° C./h; and then cooled to the final temperature.

11. The method according to claim 9, wherein, in step (5), after the thermostatic treatment, the mixture is first cooled to 97 to 115° C., the average cooling rate is 0.5 to 12° C./h, preferably 0.5 to 8° C./h; cooled further to 85 to 95° C., the average cooling rate is 2 to 15° C./h, preferably 2 to 8° C./h; and then cooled to the final temperature.

12. The method according to claim 6, comprising a fourth membrane filtration after the tertiary membrane filtration, the fourth membrane filtration is microfiltration membrane filtration or ultrafiltration membrane filtration.

13. The method according to claim 1, wherein the long-chain dicarboxylic acid is a $C_9$-$C_{18}$ dicarboxylic acid.

14. A long-chain dicarboxylic acid product, extracted by the method according to claim 1.

* * * * *